United States Patent
Kobayashi et al.

(10) Patent No.: US 11,116,261 B2
(45) Date of Patent: Sep. 14, 2021

(54) MEDICAL WORK SUPPORT SYSTEM, SURGICAL CLOTHING, AND MEDICAL APPARATUS

(71) Applicant: Toshiba Medical Systems Corporation, Otawara (JP)

(72) Inventors: Yoshimasa Kobayashi, Nasushiobara (JP); Reiko Hashimoto, Machida (JP); Takuya Sakaguchi, Utsunomiya (JP); Kyojiro Nambu, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 1156 days.

(21) Appl. No.: 14/681,674

(22) Filed: Apr. 8, 2015

(65) Prior Publication Data
US 2015/0213215 A1    Jul. 30, 2015

Related U.S. Application Data

(63) Continuation of application No. PCT/JP2013/076162, filed on Sep. 26, 2013.

(30) Foreign Application Priority Data

Oct. 11, 2012    (JP) .............................. JP2012-226308

(51) Int. Cl.
A41D 1/00    (2018.01)
A41D 13/12    (2006.01)
(Continued)

(52) U.S. Cl.
CPC ............. *A41D 1/002* (2013.01); *A41D 13/12* (2013.01); *A41D 13/1281* (2013.01);
(Continued)

(58) Field of Classification Search
None
See application file for complete search history.

(56) References Cited

U.S. PATENT DOCUMENTS 7,549,179 B1 * 6/2009 Saied ................. A41D 13/0012
                                                                 2/114
2003/0093503 A1    5/2003 Yamaki et al.
(Continued)

FOREIGN PATENT DOCUMENTS

JP    51-118322 U    9/1976
JP    2001-449 A     1/2001
(Continued)

OTHER PUBLICATIONS

Vendruscolo et al, Interfaces for Computer and Robot Assisted Surgical Systems, 2001, Information and Software Technology 43 87-96 (Year: 2001).*
(Continued)

*Primary Examiner* — Gregory Lultschik
(74) *Attorney, Agent, or Firm* — Oblon, McClelland, Maier & Neustadt, L.L.P.

(57) ABSTRACT

A medical work support system according to an embodiment includes an interface apparatus, a reception unit, and a control unit. The interface apparatus accepts operation by the user, outputs a signal corresponding to the accepted operation, and is detachably attached to wearing clothing configured to be worn by the user. The reception unit receives a signal output from the interface apparatus. The control unit executes predetermined processing based on a reception signal received by the reception unit.

7 Claims, 8 Drawing Sheets

(51) Int. Cl.
   *G16H 40/63*   (2018.01)
   *A41D 27/20*   (2006.01)
   *A61B 17/00*   (2006.01)
   *A61B 6/00*    (2006.01)
   *A61B 34/00*   (2016.01)
   *A61B 46/10*   (2016.01)
(52) U.S. Cl.
   CPC ............ *A41D 27/205* (2013.01); *A61B 6/548* (2013.01); *A61B 34/25* (2016.02); *G16H 40/63* (2018.01); *A61B 46/10* (2016.02); *A61B 2017/00199* (2013.01); *A61B 2017/00221* (2013.01)

(56) References Cited

U.S. PATENT DOCUMENTS

| | | | | |
|---|---|---|---|---|
| 2008/0091778 | A1* | 4/2008 | Ivashin | G06Q 10/10 709/204 |
| 2012/0146905 | A1* | 6/2012 | Kaneda | G06F 1/1626 345/158 |
| 2012/0186000 | A1* | 7/2012 | Raviv | A41B 1/00 2/247 |
| 2013/0173291 | A1* | 7/2013 | Kelly | G06Q 50/24 705/3 |
| 2014/0292396 | A1* | 10/2014 | Bruwer | H03K 17/955 327/517 |

FOREIGN PATENT DOCUMENTS

| | | | |
|---|---|---|---|
| JP | 2002-268622 | A | 9/2002 |
| JP | 2003-013317 | | 1/2003 |
| JP | 2003-164412 | A | 6/2003 |
| JP | 2003-223216 | | 8/2003 |
| JP | 2004-213515 | | 7/2004 |
| JP | 2005-350821 | A | 12/2005 |
| JP | 3143595 | | 7/2008 |
| JP | 2008-293361 | A | 12/2008 |
| JP | 2010-216025 | | 9/2010 |
| JP | 2011-28652 | A | 2/2011 |

OTHER PUBLICATIONS

Office Action dated Aug. 2, 2016 in Japanese Patent Application No. 2012-226308.

Japanese Office Action dated Jan. 10, 2017 in Patent Application No. 2012-226308.

Japanese Office Action dated Jun. 2017 in Patent Application No. 2012-226308.

International Search Report dated Jan. 7, 2014, for PCT/JP2013/076162 filed on Sep. 26, 2013.

International Written Opinion dated Jan. 7, 2014 for PCT/JP2013/076162 filed on Sep. 26, 2013.

Office Action dated Jul. 24, 2018 in Japanese Patent Application No. 2017-171441.

* cited by examiner

MEDICAL WORK SUPPORT SYSTEM, SURGICAL CLOTHING, AND MEDICAL APPARATUS

CROSS-REFERENCE TO RELATED APPLICATIONS

This application is a Continuation Application of PCT Application No. PCT/JP2013/076162, filed Sep. 26, 2013, and is based upon and claims the benefit of priority from Japanese Patent Application No. 2012-226308, filed Oct. 11, 2012. The entire contents of the above applications are incorporated herein by reference.

FIELD

Embodiments described herein relate generally to a medical work support system which supports medical work, surgical clothing, and a medical apparatus.

BACKGROUND

Current surgeries use various types of medical apparatuses. For example, a surgeon sometimes uses an X-ray diagnostic apparatus (so-called X-ray fluoroscopic apparatus), which captures X-ray fluoroscopic images of a patient at a predetermined frame rate and displays them in real time, to perform a surgery while grasping the internal state of the patient.

When performing a surgery, a surgeon wears surgical clothing such as a sterile gown, gloves, and cap to prevent bacterial infection between himself/herself and the patient. If the surgeon wearing surgical clothing operates an unsterile medical apparatus, bacteria adhering to the console unit and the like of the medical apparatus adhere to the surgical clothing of the surgeon. The surgeon, therefore, should not operate the medical apparatus. For this reason, in general, the surgeon informs a staff member of the details of desired operation, and the staff member operates the console unit. In this case, the surgeon may not accurately inform the staff member of information. This may hinder a smooth surgical procedure.

Even if, for example, the console unit of the medical apparatus is wrapped with a sterile bag to prevent bacteria from adhering from the console unit, it is cumbersome for the surgeon to move to the position of the console unit.

In addition to these, there are various problems in the operation of the medical apparatus in surgeries.

DETAILED DESCRIPTION

In general, according to one embodiment, a medical work support system includes an interface apparatus, a reception unit, and a control unit. The interface apparatus accepts operation by the user, outputs a signal corresponding to the accepted operation, and is detachably attached to wearing clothing configured to be worn by the user. The reception unit receives a signal output from the interface apparatus. The control unit executes predetermined processing based on a reception signal received by the reception unit.

Several embodiments will be described with reference to the accompanying drawings.

First Embodiment

The first embodiment exemplifies a medical work support system for supporting the operation of an X-ray diagnostic apparatus as a type of medical apparatus and surgical clothing which provides a usage environment suitable for the medical work support system.

[Medical Work Support System]

The first embodiment exemplifies a medical work support system for supporting the operation of an X-ray diagnostic apparatus as a type of medical apparatus and surgical clothing which provides a usage environment suitable for the medical work support system.

The medical work support system will be described first with reference to FIGS. 1, 2, 3, and 4.

Figure 1:
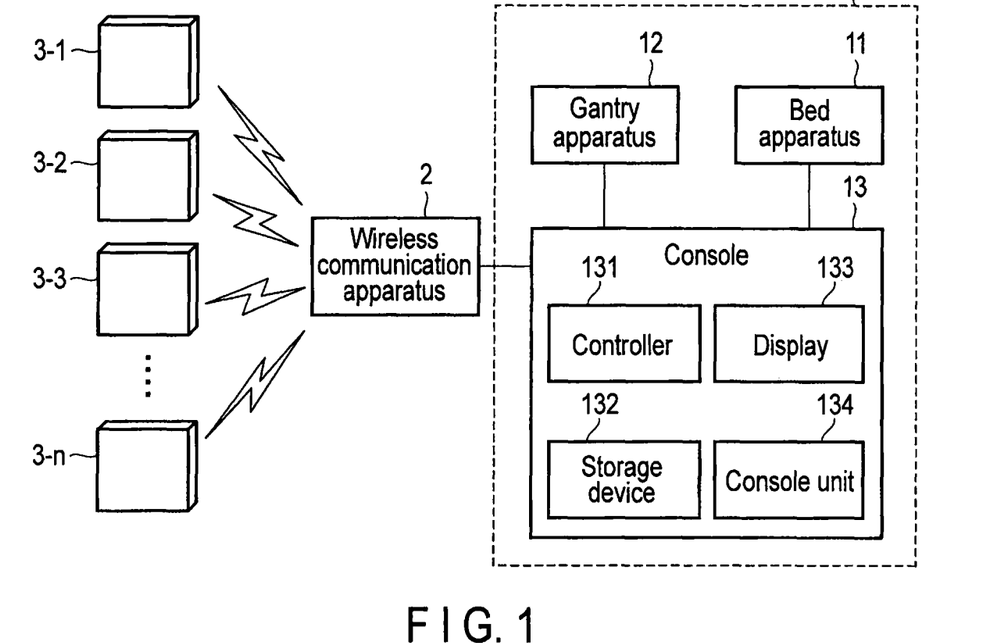
FIG. 1 is a block diagram showing the hardware configuration of a medical work support system according to the first embodiment.

FIG. 1 is a block diagram showing the hardware configuration of the medical work support system according to this embodiment. The medical work support system includes an X-ray diagnostic apparatus 1 installed in an operating room, a wireless communication apparatus 2, and n user interface apparatuses 3-1, 3-2, 3-3, . . . , 3-n. In the following description, the user interface apparatuses 3-1, 3-2, 3-3, . . . , 3-n will each be simply referred to as a user interface apparatus 3 when not specifically discriminated.

The X-ray diagnostic apparatus 1 includes a bed apparatus 11, a gantry apparatus 12, and a console 13 connected to the bed apparatus 11 and the gantry apparatus 12.

The bed apparatus 11 includes a top on which a patient is placed and a moving mechanism for moving the top in the horizontal and vertical directions relative to the placement surface.

The gantry apparatus 12 includes a high voltage generator which generates a high voltage, an X-ray tube which generates X-rays upon reception of the high voltage generated by the high voltage generator, an X-ray stop device which narrows the X-rays generated by the X-ray tube to a predetermined region, and an X-ray detection apparatus which detects X-rays and outputs detection data.

The console 13 includes a controller (control unit) 131, a storage device 132, a display 133, and a console unit 134. The controller 131 includes a processor and a memory. The processor implements various types of processing by executing computer programs. For example, when performing X-ray fluoroscopy, the controller 131 generates an X-ray fluoroscopic image based on the detection data output from the X-ray detector of the gantry apparatus 12. The storage device 132 is an auxiliary storage device such as an HDD (Hard Disk Drive) or SSD (Solid State Drive). The storage device 132 stores an operating system, various types of application files, the X-ray fluoroscopic images generated by the controller 131, and the like. The display 133 is an LCD (Liquid Crystal Display), which displays the X-ray fluoroscopic images generated by the controller 131, various types of GUIs (Graphical User Interfaces), and the like. The console unit 134 includes a mouse, keyboard, buttons, trackball, and joystick which are used by the operator of the X-ray diagnostic apparatus 1 to input various types of commands and information.

The wireless communication apparatus 2 and the user interface apparatus 3 perform wireless communication via, for example, radio waves. The wireless communication apparatus 2 is connected to the console 13. The wireless communication apparatus 2 includes a transmission circuit which modulates a signal to be transmitted to the user interface apparatus 3, an antenna which transmits radio waves corresponding to the transmission signal modulated by the transmission circuit to the user interface apparatus 3 and outputs a reception signal upon receiving the radio waves transmitted from the user interface apparatus 3, and a reception circuit which demodulates the reception signal output from the antenna. The wireless communication apparatus 2 outputs the demodulated reception signal to the console 13.

Figure 2:
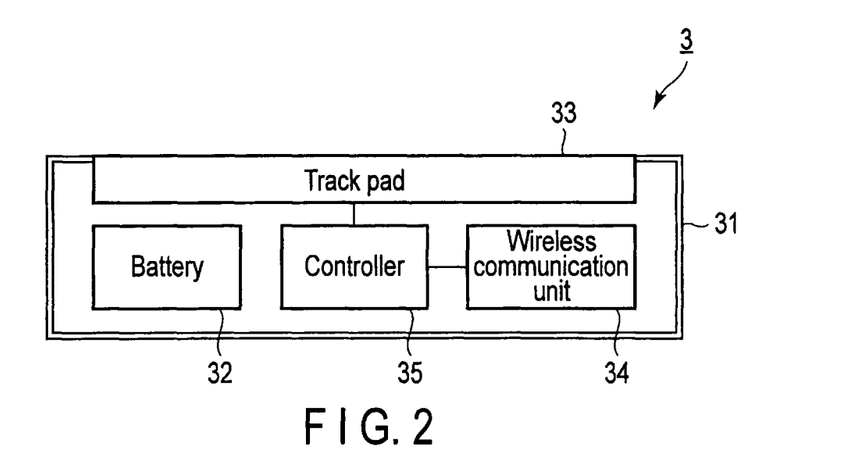
FIG. 2 is a block diagram showing the hardware configuration of a user interface apparatus according to the first embodiment.

FIG. 2 shows the hardware configuration of the user interface apparatus 3. The user interface apparatus 3 includes a housing 31, a battery 32 incorporated in the housing 31, a track pad 33, a wireless communication unit 34, and a controller 35.

The housing 31 has a shape compact enough to allow the user to hold the apparatus with one hand while operating it with the other hand. The battery 32 supplies operating power to the track pad 33, the wireless communication unit 34, and the controller 35.

The operation surface of the track pad 33 is exposed from the housing 31. As the track pad 33, it is possible to use, for example, an electrostatic capacitance type track pad. When the user touches the operation surface of the track pad 33 of this type with his/her finger or the like, the track pad 33 detects a slight change in electrostatic capacitance caused at the contact position and outputs a signal corresponding to the detection position to the controller 35.

The wireless communication unit 34 includes a transmission circuit which modulates data to be transmitted to the wireless communication apparatus 2, an antenna which transmits radio waves corresponding to the transmission signal modulated by the transmission circuit to the wireless communication apparatus 2 and outputs a reception signal upon receiving the radio waves transmitted from the wireless communication apparatus 2, and a reception circuit which demodulates the reception signal output from the antenna.

The controller 35 includes a processor and a memory. The controller 35 implements various types of processing by executing computer programs using this processor. For example, the controller 35 calculates the coordinates of an operation position on the operation surface based on the signal input from the track pad 33 and outputs a transmission signal indicating the calculated coordinates to the wireless communication unit 34. The wireless communication unit 34 transmits radio waves corresponding to this transmission signal to the wireless communication apparatus 2. The controller 35 calculates and transmits such coordinates at, for example, a detection rate of about several 10 times per sec. The controller 35 sometimes executes processing based on the reception signal generated by the wireless communication unit 34.

Note that the controller 35 lets the transmission signal output from the wireless communication unit 34 contain the identifier of the user interface apparatus 3 (self-apparatus). This makes it possible to recognize the transmission source of a signal on the wireless communication apparatus 2 or console 13.

When using the X-ray diagnostic apparatus 1 in a surgery, the surgeon or his/her assistant sometimes needs to operate the console unit 134. When, for example, wanting to change the X-ray irradiation field by operating the X-ray stop device during a surgery, the surgeon or his/her assistant needs to perform the operation associated with changing the irradiation field with the console unit 134. In addition, when wanting to change various conditions associated with X-rays, e.g., a tube voltage and a tube current, the surgeon or his/her assistant needs to perform operation associated with changing the conditions with the console unit 134.

The medical work support system according to this embodiment allows the user to also perform such work, which has been performed by operating the console unit 134, by using the user interface apparatus 3. In addition, the medical work support system gives an operation right to one of the user interface apparatuses 3-1 to 3-$n$ to prevent operational confusion among the plurality of user interface apparatuses 3.

Figure 3:
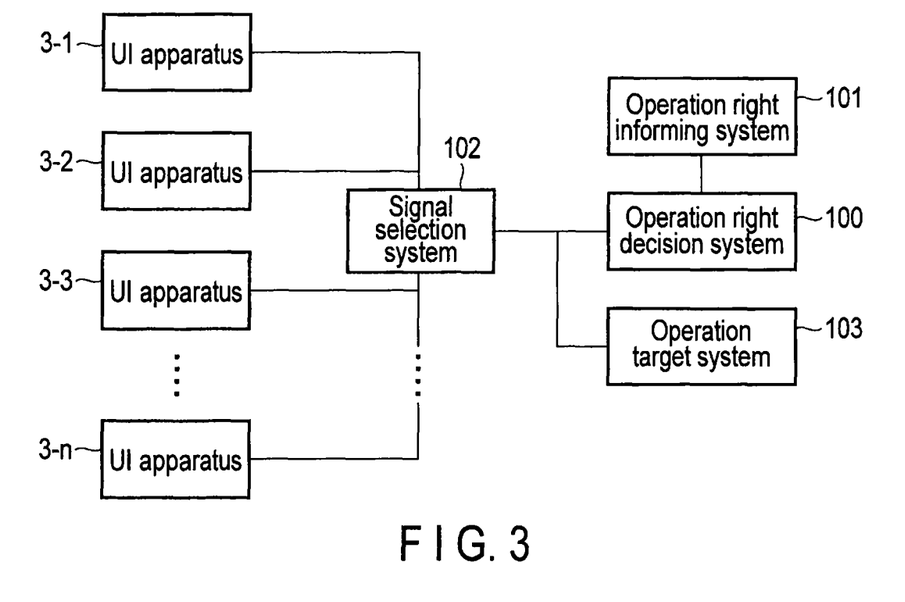
FIG. 3 is a block diagram of the medical work support system according to the first embodiment.

FIG. 3 is a block diagram for the implementation of these functions. The medical work support system according to this embodiment includes an operation right decision system 100, an operation right informing system 101, and a signal selection system 102. Each of the systems 100 to 102 may be implemented by using any elements included in the medical work support system. For example, each of the systems 100 to 102 can be implemented by elements (not shown) such as the processor, memory, display, and input device included in the wireless communication apparatus 2 or can be implemented by elements such as the controller 131, the storage device 132, display 133, console unit 134, and the like included in the console 13. In addition, each of the systems 100 to 102 can be implemented by a combination of elements included in the wireless communication apparatus 2 and elements included in the console 13.

Note that an operation target system 103 shown in FIG. 3 is a system (apparatus) for which the user operates the user interface (UI) apparatus 3. In this embodiment, the console 13 of the X-ray diagnostic apparatus 1 corresponds to the operation target system 103.

The operation right decision system 100 decides the user interface apparatus 3 having an operation right for the operation target system from the user interface apparatuses 3-1 to 3-*n*.

The operation right informing system 101 makes a notice of the user interface apparatus 3 having the operation right.

The signal selection system 102 selects the signal, transmitted from the user interface apparatus 3 having the operation right, from the signals which the wireless communication apparatus 2 receives from the user interface apparatuses 3-1 to 3-*n*. As described above, the signal transmitted from the user interface apparatus 3 includes the identifier of the user interface apparatus 3 as the transmission source. The signal selection system 102 selects the signal transmitted from the user interface apparatus 3 having the operation right by referring to this identifier. The signal selection system 102 outputs the selected signal to the operation target system 103 and the operation right decision system 100.

The operation target system 103 (i.e., the console 13) executes processing corresponding to the signal input from the signal selection system 102.

Assume that the user has performed the dragging operation of tracing the track pad 33 of the user interface apparatus 3 with his/her finger. The user interface apparatus 3 transmits signals indicating the coordinates detected in the process of the above dragging operation to the signal selection system 102 at the above transmission rate. While these signals are input to the operation target system 103, the controller 131 of the console 13 repeats the processing of moving the cursor displayed in a window on the display 133 in a direction and by a distance corresponding to the vector whose start point is the coordinates indicated by a given signal and whose end point is the coordinates indicated by the next signal. It is possible to adjust the X-ray irradiation field by this dragging operation. In this case, for example, the controller 131 of the console 13 classifies the direction indicated by the above vector as either the positive direction or the negative direction. Upon classifying the direction as the positive direction, the controller 131 controls the X-ray stop device to expand the irradiation field by the distance corresponding to the above vector. Upon classifying the direction as the negative direction, the controller 131 controls the X-ray stop device to narrow the irradiation field by the distance corresponding to the above vector. In addition to the adjustment of the irradiation field, the user can implement various types of operations accompanying the designation of directions by dragging operation on the track pad 33.

Assume that the user has performed the tapping operation of momentarily touching the track pad 33 of the user interface apparatus 3. Upon receiving a signal corresponding to this tapping operation, the controller 131 of the console 13 executes the processing preset in the GUI displayed at a position at which it overlaps the above cursor in a window on the display 133.

In addition to these, various types of correspondence relations can be defined between operations on the track pad 33 and processes executed by the operation target system 103.

Figure 4:
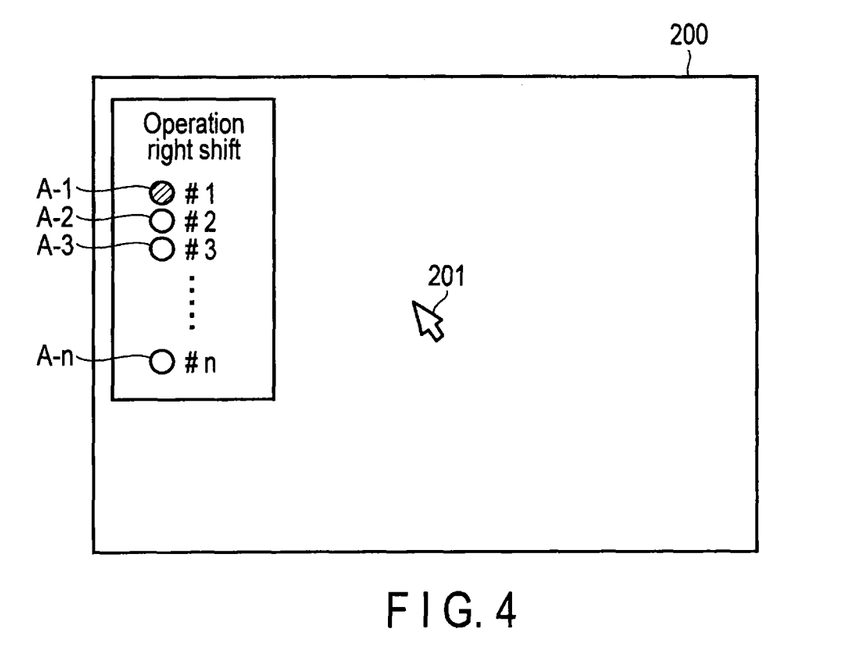
FIG. 4 is a view showing a window example displayed by an operation right decision system according to the first embodiment.

The operation right decision system 100 according to this embodiment decides the user interface apparatus 3 having an operation right by using, for example, a window 200 shown in FIG. 4. The window 200 is displayed on, for example, the display 133, and includes display areas A-1, A-2, A-3, . . . , A-*n* provided in correspondence with the user interface apparatuses 3-1 to 3-*n* and a cursor 201. The identifiers (#1, #2, #3, . . . , #n) of the user interface apparatuses 3-1 to 3-*n* corresponding to the display areas A-1 to A-*n* are added to the right sides of the display areas A-1 to A-*n*. In the following description, the display areas A-1, A-2, A-3, . . . , A-*n* will each be simply referred to as a display area A when not specifically discriminated.

The operation right decision system 100 moves the cursor 201 in accordance with the signal transmitted by the user interface apparatus 3 having an operation right in response to the dragging operation on the track pad 33. Upon receiving a signal indicating tapping operation on the track pad 33 from the user interface apparatus 3 having an operation right while the cursor 201 is placed on any one of the display areas A-1 to A-*n*, the operation right decision system 100 decides the user interface apparatus 3 corresponding to the display area A as the user interface apparatus 3 having an operation right.

It is possible to shift the operation right by using the user interface apparatus 3 having no operation right. In this case, a special operation on the track pad 33 which is to be performed to request for an operation right is determined in advance. As a special operation, it is preferable to use an operation clearly different from usual operations, including, for example, rubbing the track pad 33 five or more times in a predetermined direction within 2 sec. Upon determining that the user has performed the above special operation on the user interface apparatus 3 based on the signal transmitted from the user interface apparatus 3 having no operation right, the signal selection system 102 transmits the identifier of the user interface apparatus 3 to the operation right decision system 100. Upon receiving this identifier, the operation right decision system 100 decides the user interface apparatus 3 indicated by the identifier as the user interface apparatus 3 having an operation right.

Assume that no operation has been performed on the user interface apparatus 3 having an operation right over a predetermined time, and some operation has been executed on one of the user interface apparatuses 3. In this case, the operation right decision system 100 gives an operation right to the user interface apparatus 3 on which the operation has been executed. More specifically, the operation right decision system 100 compares the time (to be referred to as the operation non-input time hereinafter) during which no operation is input to the user interface apparatus 3 having an operation right with a predetermined time. Provided that the operation non-input time exceeds the predetermined time, the operation right decision system 100 specifies the user interface apparatus operated first. The operation right decision system 100 gives an operation right to a specified one of the plurality of user interface apparatuses 3. The predetermined time is stored in, for example, the storage device 132 or a memory (not shown). In other words, provided that no operation has been input to a user interface apparatus having an operation right over a predetermined time, the operation right decision system 100 gives an operation right to the user interface apparatus 3 operated first after the operation non-input time exceeds the predetermined time.

The operation right informing system 101 according to this embodiment makes a notice of the user interface apparatus 3 having an operation right by using the window 200. More specifically, the operation right informing system 101 makes the display area A, corresponding to the user interface apparatus 3 decided by the operation right decision system 100 as having an operation right in the above procedure, have a color different from that of the remaining display areas A. FIG. 4 shows a case in which the user interface apparatus 3-1 corresponding to "#1" has an operation right, and the display area A-1 is hatched to express that it has a color different from that of the remaining display areas A-2 to A-n.

Note that the operation right informing system 101 may make a notice of the user interface apparatus 3 having an operation right by another mode using a display, turning on a lamp, outputting sound from a loudspeaker, or the like.

According to the medical work support system having the above arrangement, the doctor can remotely control the operation target system 103 by using the user interface apparatus 3 in a sterile state (i.e., while maintaining a sterile state). This makes it possible to smoothly proceed with a surgery. In addition, the medical work support system gives an operation right to one of the plurality of user interface apparatuses 3-1 to 3-n, and outputs only a signal from the user interface apparatus 3 given this operation right to the operation target system 103. Even if, therefore, a plurality of users simultaneously operate the plurality of user interface apparatuses 3-1 to 3-n, it is possible to prevent the operation target system 103 from malfunctioning. In addition, since the operation right informing system 101 makes a notice of the user interface apparatus 3 having an operation right, it is possible to easily grasp the user of the user interface apparatus 3 having the operation right.

[Surgical Clothing]

Figure 6:
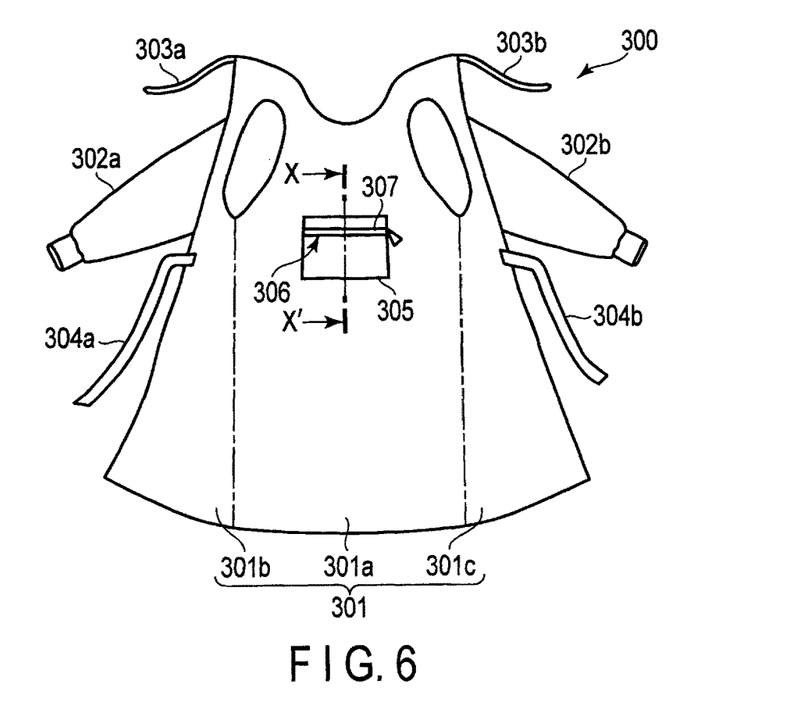
FIG. 6 is a schematic view showing the reverse surface side of the sterile gown according to the first embodiment.
Figure 7:
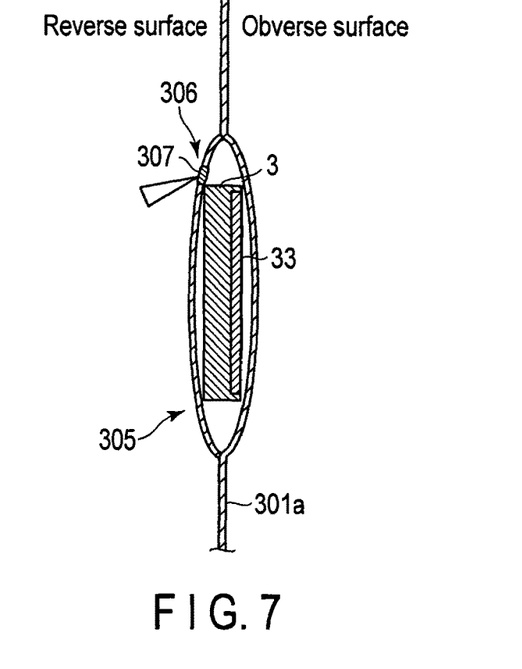
FIG. 7 is a sectional view taken along X-X' in FIG. 6.

Surgical clothing (wearing clothing or sterile clothing) which a surgeon and his/her assistant can wear in the use of the medical work support system will be described subsequently with reference to FIGS. 5, 6, and 7.

Figure 5:
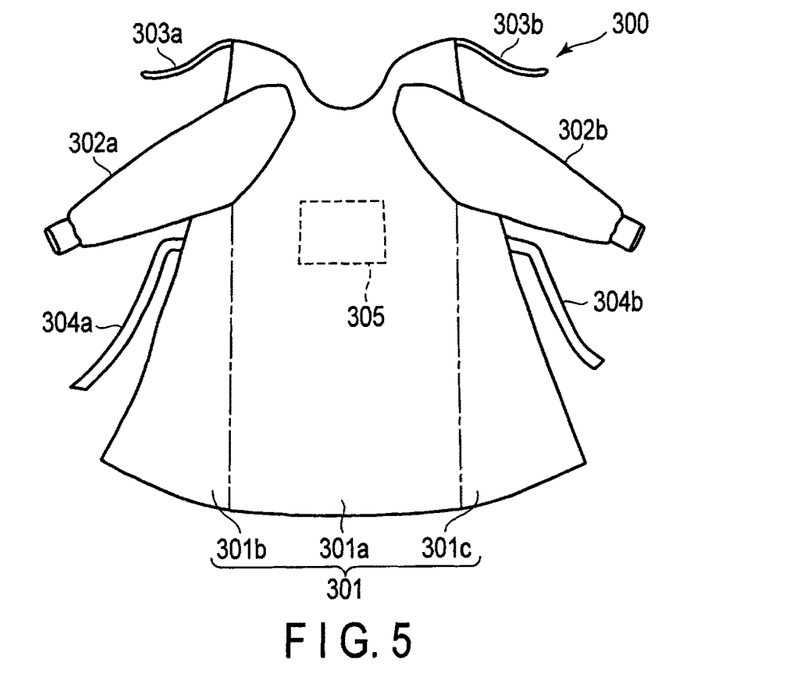
FIG. 5 is a schematic view showing the obverse surface side of a sterile gown according to the first embodiment.

FIG. 5 is a schematic view showing the obverse surface side of a sterile gown 300 as a type of surgical clothing. FIG. 6 is a schematic view showing the reverse surface side of the sterile gown 300. The sterile gown 300 includes a body part 301 having a front body 301a, a back body right half part 301b, and a back body left half part 301c which are formed by one cloth and a right sleeve 302a and a left sleeve 302b respectively sewed to upper parts of the body part 301. The body part 301, the right sleeve 302a, and the left sleeve 302b are formed from, for example, unwoven cloth made of a polyethylene-based resin as a material. The body part 301, the right sleeve 302a, and the left sleeve 302b constitute a surgical clothing main body.

A pair of left and right strings 303a and 303b are sewed to the upper portion of the body part 301 which corresponds to the neckline, and a pair of left and right band pieces 304a and 304b are sewed to the middle portion of the body part 301. The user wears the sterile gown 300 so as to close the back side by tying the strings 303a and 303b around the neck and tying the band pieces 304a and 304b around the waist.

A pocket 305 for accommodating the user interface apparatus 3 is provided on the back surface of the front body 301a. FIG. 7 is a sectional view taken along X-X' of the pocket 305.

The pocket 305 is attached to the back surface side of the front body 301a by, for example, sewing edge portions of a cloth piece having a predetermined size to the back surface side of the front body 301a. The pocket 305 is provided with an insertion opening 306 into which the user interface apparatus 3 is inserted. The insertion opening 306 is provided with a line fastener 307 for opening and closing the opening. Note that the insertion opening 306 may be provided with a button or surface fastener instead of the line fastener 307 to make the insertion opening 306 openable/closable.

When starting a surgery using the X-ray diagnostic apparatus 1, the surgeon and his/her assistant each insert the user interface apparatus 3 into the pocket 305, with the operation surface of the track pad 33 facing the obverse surface side, and closes the line fastener 307.

Subsequently, the surgeon and his/her assistant wash their arms from the fingertips to the elbows with sterile water (or controlled tap water) and an antiseptic solution. The surgeon and his/her assistant wear lead protective clothing. The surgeon and his/her assistant each wear the sterile gown 300 on the lead protective clothing with the help of a helper. The surgeon and his/her assistant also wear sterile gloves and caps.

It is possible to operate the user interface apparatus 3 accommodated in the pocket 305 from the obverse surface side through the front body 301a. In other words, the thicknesses of the front body 301a and sterile gloves worn by the surgeon and the sensitivity of the track pad 33 are designed to such an extent that the user can operate the user interface apparatus 3 while it is accommodated in the pocket 305.

As described above, according to the sterile gown 300 having the above arrangement, it is possible to operate the user interface apparatus 3 from the obverse surface side of the surgical clothing main body without directly touching the apparatus 3 while the user interface apparatus 3 is accommodated in the pocket 305. Therefore, the user can operate the operation target system 103 without considering the adhesion of bacteria from the user interface apparatus 3.

The surgeon can operate the operation target system 103 with his/her own hand without moving to the installation position of the console unit 134 or instructing the assistant to operate the console unit 134. This makes it possible to expect a smooth surgery procedure.

Second Embodiment

The second embodiment will be described. The same reference numerals denote the same constituent elements as those of the first embodiment, and a repetitive description will be omitted.

When remotely controlling the console 13 by using the user interface apparatus 3 disclosed in the first embodiment, the vertical and horizontal directions viewed from the operator sometimes coincide and sometimes conflict with the vertical and horizontal directions of the user interface apparatus 3 depending on the mode of use of the user interface apparatus 3. This leads to erroneous operation by the user. This embodiment therefore discloses a means for solving the problem of the direction discrepancy caused depending on the two modes of use respectively shown in FIGS. 8A and 8B.

Figure 8A:
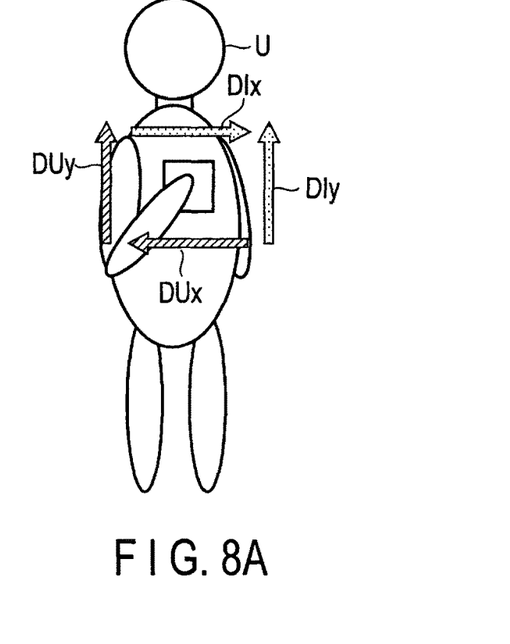
FIG. 8A is a view for explaining the mode of use of a user interface apparatus according to the second embodiment.
Figure 8B:
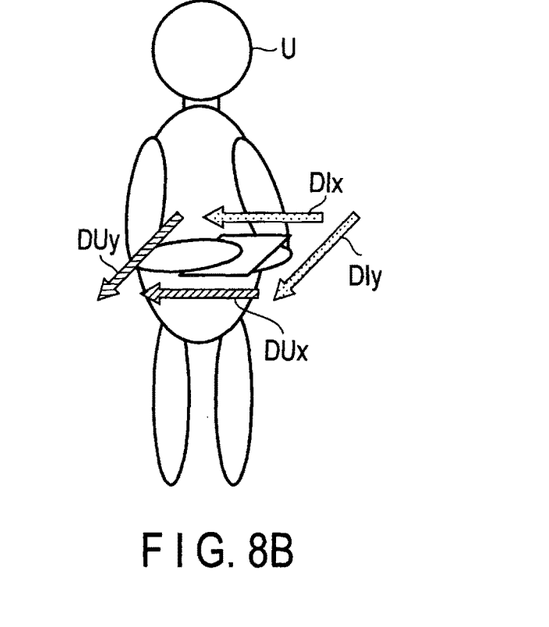
FIG. 8B is a view for explaining the mode of use of a user interface apparatus according to the second embodiment.

FIG. 8A schematically shows the mode of use of a user interface apparatus 3 by a user U while it is accommodated in the pocket 305 of the sterile gown 300 disclosed in the first embodiment, with the operation surface of the track pad 33 facing the obverse surface side. FIG. 8B schematically shows the mode of use of the user interface apparatus 3 by the user U while he/she holds the user interface apparatus 3 with his/her hand or the user interface apparatus 3 is attached to a front arm portion of the sterile gown 300. Note that when attaching the user interface apparatus 3 to the front arm portion of the sterile gown 300, the pocket 305 is provided at a proper position on the reverse side of a right sleeve 302a or left sleeve 302b. The user interface apparatus 3 is accommodated in the pocket while the operation surface of the track pad 33 faces the obverse surface side. That is, the user interface apparatus 3 is detachably attached to the wearing clothing.

Assume that in either of the modes of use in FIGS. 8A and 8B, a vertical direction DUy viewed from the user coincides with a vertical direction DIy of the user interface apparatus 3. In this case, referring to FIG. 8A, a horizontal direction DUx viewed from the user is opposite to a horizontal direction DIx of the user interface apparatus 3. In contrast to this, referring to FIG. 8B, the horizontal direction DUx viewed from the user coincides with the horizontal direction DIx of the user interface apparatus 3.

As described above, in this case, the horizontal direction DUx viewed from the user sometimes coincides and sometimes conflicts with the horizontal direction DIx of the user interface apparatus 3 depending on the mode of use of the user interface apparatus 3. This hinders smooth operation using the user interface apparatus 3.

Figure 9:
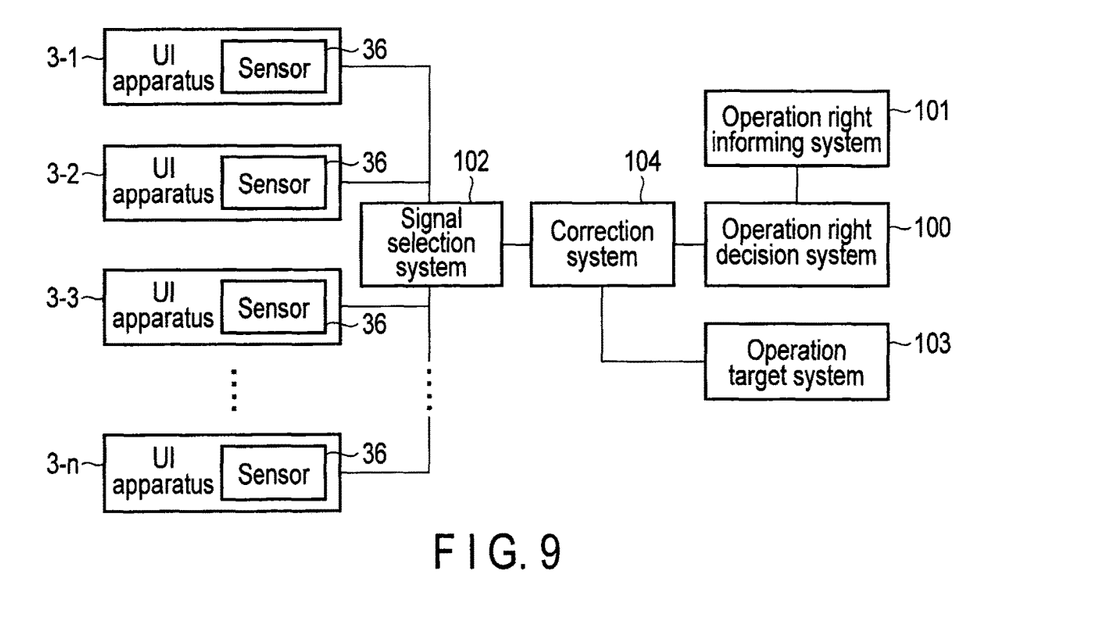
FIG. 9 is a functional block diagram of a medical work support system according to the second embodiment.

In order to handle this problem, in this embodiment, as shown in FIG. 9, a correction system 104 is interposed between a signal selection system 102 and an operation target system 103. In addition, the user interface apparatus 3 is provided with a sensor 36 for detecting the posture of the user interface apparatus 3. As the sensor 36, it is possible to use, for example, a 3-axis acceleration sensor which detects a gravitational acceleration.

A controller 35 of the user interface apparatus 3 according to this embodiment outputs a transmission signal representing the acceleration detected by the sensor 36 and the identifier of the user interface apparatus 3 (self-apparatus) to a wireless communication unit 34 at a predetermined timing. The wireless communication unit 34 which has received this transmission signal transmits radio waves corresponding to the signal to a wireless communication apparatus 2. The above predetermined timing may be, for example, predetermined time intervals or the time when the controller 35 detects operation on the track pad 33.

The wireless communication apparatus 2 receives the above signal including the acceleration which is transmitted from the user interface apparatus 3 having an operation right. This signal then passes through the signal selection system 102 and is transmitted to the correction system 104. Upon receiving this signal, the correction system 104 discriminates either of the modes in FIGS. 8A and 8B in which the user interface apparatus 3 is used, by comparing the acceleration represented by the signal with a predetermined threshold.

Upon determining as a result of this determination that the user interface apparatus 3 is used in the mode in FIG. 8A, the correction system 104 performs the correction of interchanging the horizontal direction for the signal input from the signal selection system 102, and outputs the signal after this correction to the operation target system 103.

Figure 10:
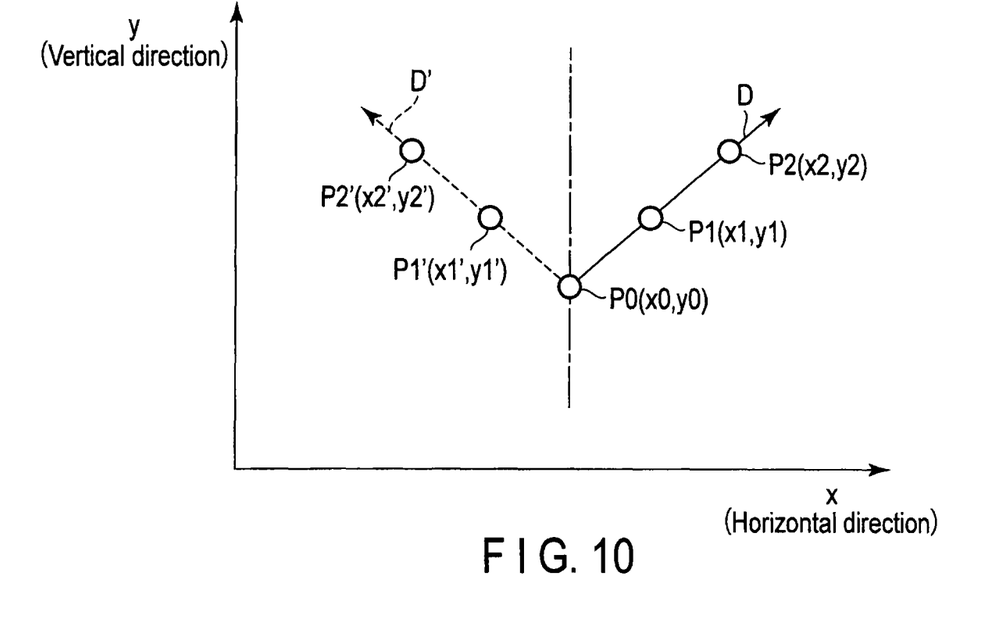
FIG. 10 is a graph for explaining an example of correction by a correction system according to the second embodiment.

An example of correction by the correction system 104 will be described with reference to FIG. 10. FIG. 10 shows coordinates Pi(xi, yi) detected by the user interface apparatus 3 at the time of the operation of the track pad 33 and coordinates Pi'(xi', yi') after correction by the correction system 104. Note that "xi" and "xi'" represent components concerning the horizontal direction of the user interface apparatus 3, and "yi" and "yi'" represent components concerning the vertical direction of the user interface apparatus 3. The suffix i represents the order of detection of coordinates with 0 being the start point (the starting point of dragging operation).

A solid line arrow D passing through coordinates P0, P1, and P2 represents the locus of the coordinates represented by the signal input from the signal selection system 102 to the correction system 104 at the time of dragging operation on the track pad 33. The correction system 104 obtains coordinates Pi' symmetric to coordinates Pi input from the signal selection system 102 after the coordinates P0 as the start point with respect to a straight line (indicated by the one-dot dashed line) which passes through the coordinates P0 and is perpendicular to the x-axis. The correction system 104 outputs the signal representing the coordinates Pi' to the operation target system 103 in place of the coordinates Pi. Note that in this case, xi'=2×0−xi' and yi'=yi.

A broken line arrow D' passing through coordinates P0, P1', and P2' represents the locus of the coordinates represented by the signal output from the correction system 104 to the operation target system 103. Comparing the arrows D and D' will reveal that the horizontal direction (x direction) is reversed.

In contrast, if the correction system 104 discriminates that the user interface apparatus 3 is used in the mode in FIG. 8B, by comparing the acceleration represented by the above signal including the acceleration, which is transmitted from the user interface apparatus 3, with the predetermined threshold, the correction system 104 does not perform the correction described with reference to FIG. 10. In this case, the correction system 104 outputs the signal from the signal selection system 102 to the operation target system 103 without any change.

The medical work support system according to this embodiment performs correction such that the direction designated by operation on the user interface apparatus 3 coincides with the vertical and horizontal directions viewed from the user regardless of the posture of the user interface apparatus 3. This makes it possible to operate the operation target system 103 more smoothly and prevent operation errors.

Third Embodiment

The third embodiment will be described. The same reference numerals denote the same constituent elements as those of the first and second embodiments, and a repetitive description will be omitted.

When using the user interface apparatus 3 while it is accommodated in the pocket 305 of the sterile gown 300 disclosed in the first embodiment, the following problem arises.

Figure 11:
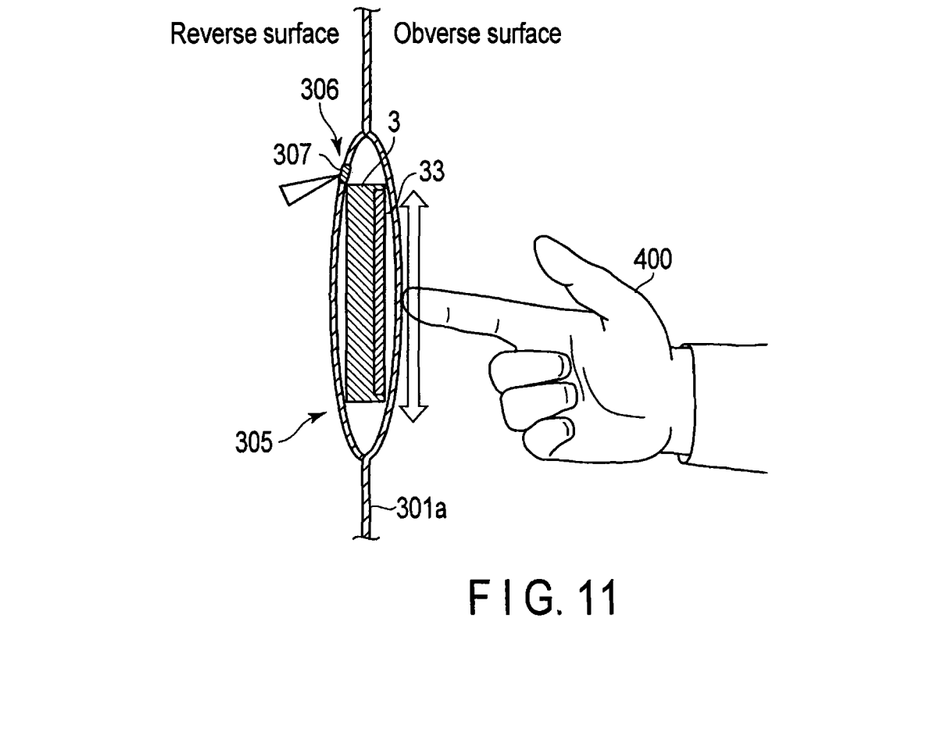
FIG. 11 is a view showing the manner of operating a user interface apparatus accommodated in a pocket of a sterile gown according to the third embodiment.

Since large frictional resistance is generated between general sterile gloves for surgery and the obverse surface of a sterile gown 300, they do not easily slide on each other. When, therefore, operating a user interface apparatus 3 in a pocket 305 shown in FIG. 11 by sliding a fingertip of a hand wearing a sterile glove 400 on the surface of the sterile gown 300, the user cannot easily move his/her finger due to frictional resistance, thereby hindering smooth operation.

This embodiment therefore discloses the sterile gown 300 configured to improve the operability of the user interface apparatus 3 in the pocket 305.

Figure 12:
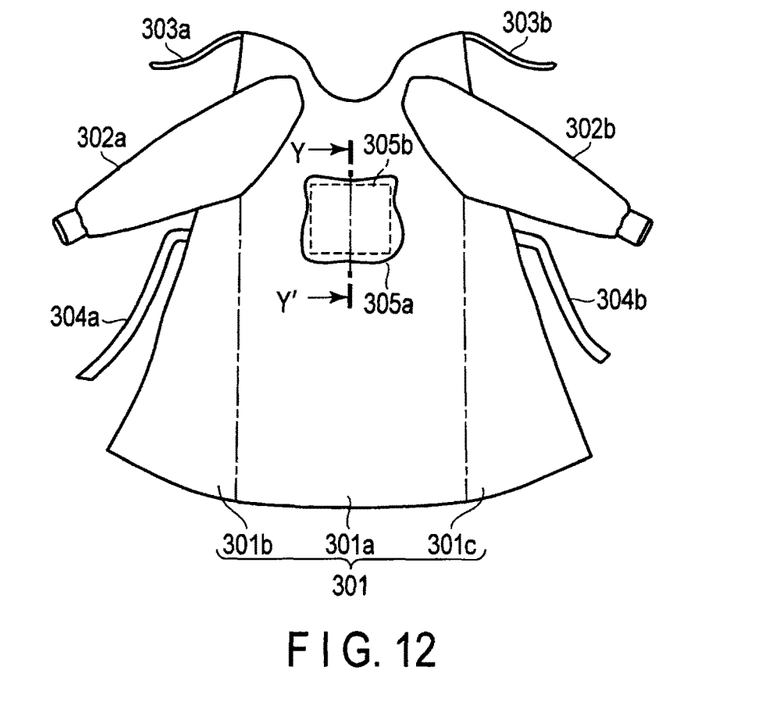
FIG. 12 is a schematic view showing the obverse surface side of the sterile gown according to the third embodiment.
Figure 13:
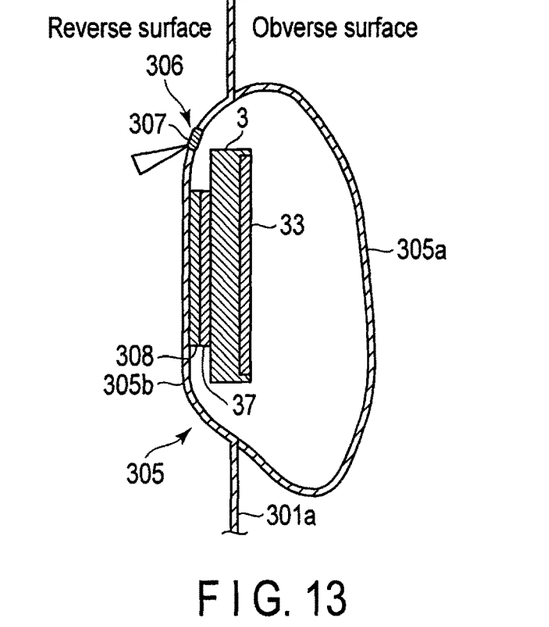
FIG. 13 is a sectional view taken along Y-Y' in FIG. 12 according to the third embodiment.

FIG. 12 is a schematic view showing the obverse surface side of the sterile gown 300 according to this embodiment. FIG. 13 is a sectional view taken along Y-Y' in FIG. 12. The reverse surface side of the sterile gown 300 has the same shape as that shown in FIG. 6. The sterile gown 300 according to this embodiment differs in the arrangement of the pocket 305 from that described in the first embodiment.

The pocket 305 includes a cloth piece 305a forming the obverse surface side and a cloth piece 305b forming a reverse surface side. The cloth pieces 305a and 305b are formed from unwoven cloth made of a polyethylene-based resin as a material like, for example, a body part 301 and right and left sleeves 302a and 302b.

An edge portion of the cloth piece 305a and an edge portion of the cloth piece 305b are sewed to a front body 301a at the same position. When the cloth piece 305a is set to have a larger area than that of the cloth piece 305b, the obverse surface side of a pocket 305 is made sag as shown in FIG. 13.

The inside of the pocket 305 is provided with a fixing mechanism for fixing a user interface apparatus 3. FIG. 13 exemplifies a surface fastener 308 as a fixing mechanism which is fixed to the cloth piece 305b In this case, the reverse surface (the surface on the opposite side to the operation surface of a track pad 33) of the user interface apparatus 3 is provided with a surface fastener 37 which engages with the surface fastener 308. Engaging the surface fastener 308 with the surface fastener 37 will fix the user interface apparatus 3 to the cloth piece 305b.

Figure 14:
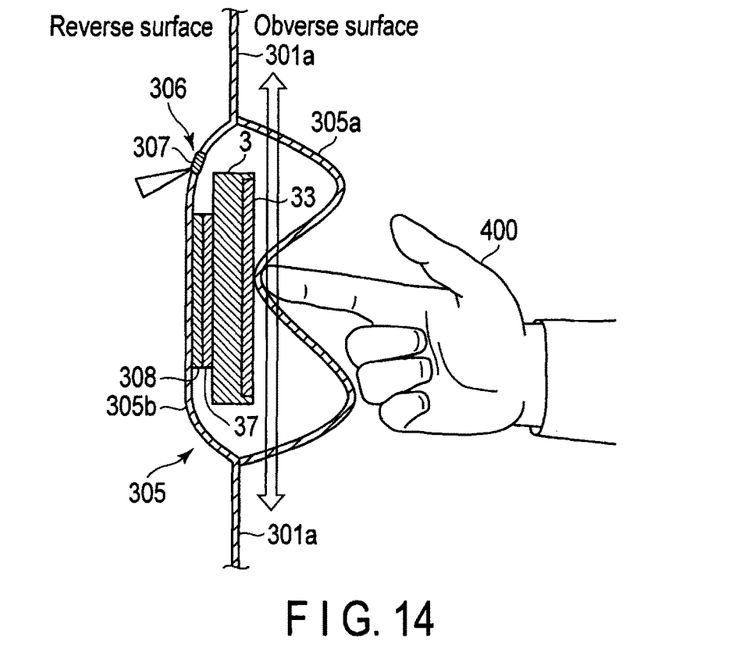
FIG. 14 is a view showing the manner of operating the user interface apparatus accommodated in the pocket of the sterile gown according to the third embodiment.

FIG. 14 is a schematic view showing the manner of using the user interface apparatus 3 accommodated in the pocket 305 of the sterile gown 300. When operating the user interface apparatus 3 from the obverse surface side of the pocket 305 with a hand wearing the sterile glove 400, the user can perform smooth operation within the range in which the contact position of the fingertip on the cloth piece 305b receives no tension from an edge portion. In this embodiment, in particular, since the obverse surface side of the pocket 305 sags, this range is wide. In addition, since the user interface apparatus 3 is fixed to the reverse surface side of the pocket 305 with the fixing mechanism, the position of the user interface apparatus 3 is difficult to shift. This makes it possible to perform operation more smoothly.

Note that the ratio between the area of the cloth piece 305a and the area of the cloth piece 305b is, for example, approximately 1:2. Note however that an area ratio that allows easy operation of the user interface apparatus 3 may be empirically, experimentally, or logically found and used at the stage of execution.

Fourth Embodiment

The fourth embodiment will be described. The same reference numerals denote the same constituent elements as those of the first and second embodiments, and a repetitive description will be omitted.

When the user uses the user interface apparatus 3 while accommodating it in the pocket 305 of the sterile gown 300 disclosed in the first and third embodiments, at least the sterile glove 400 and the obverse surface side of the pocket 305 are interposed between a finger of the user and the track pad 33. Therefore, a change in the electrostatic capacitance of the track pad 33 is smaller than that when the user directly operates the track pad 33 with his/her finger. There is therefore a fear that the user cannot perform desired input operation.

This embodiment discloses a sterile gown 300 and a sterile glove 400 which are configured to operate a track pad 33 of a user interface apparatus 3 accommodated in a pocket 305 with high sensitivity.

Figure 15:
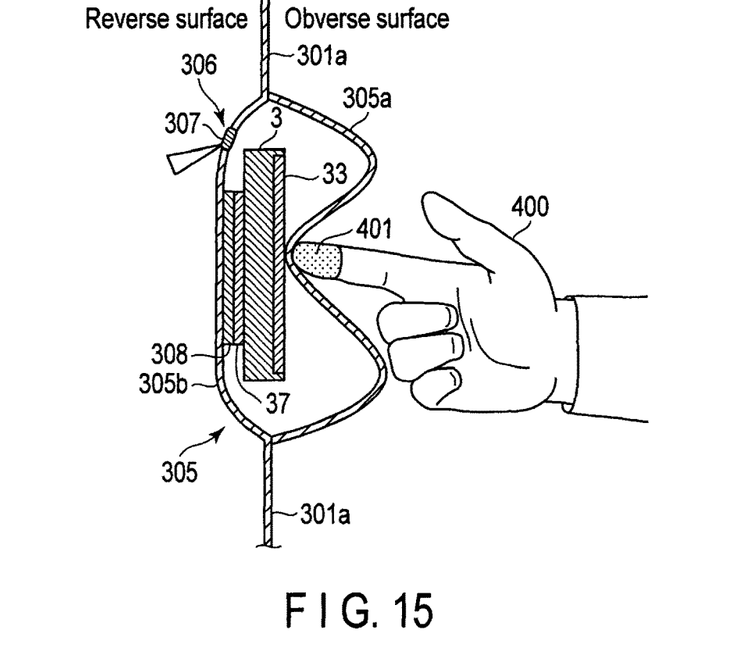
FIG. 15 is a view for explaining the arrangements of a sterile gown and sterile glove according to the fourth embodiment.

FIG. 15 is a view for explaining the arrangements of the sterile gown 300 and sterile glove 400 according to this embodiment. The sterile gown 300 according to this embodiment is configured such that a cloth piece 305a of the obverse surface side of the pocket 305 disclosed in the third embodiment is made of a material having electrical conductivity. A fingertip portion 401 of the sterile glove 400 is made of a material having electrical conductivity. These components can be made of the same material as that used for protective bags used to protect, for example, hard disks, substrates, and the like against static electricity. A material of this type has a multilayer structure with a metal layer formed by rolling aluminum being sandwiched between a polyester film and a polyethylene film and exhibits good electrical conductivity.

If the obverse surface side of the pocket 305 and the fingertip of the sterile glove 400 are formed by using a material having electrical conductivity, a change in electrostatic capacitance easily occurs at the position at which the user touches the track pad 33 with his/her finger. This improves the detection accuracy of operation on the user interface apparatus 3 and operability.

Modification

The arrangements disclosed in the first to fourth embodiments can be variously modified.

For example, the medical work support system may be configured to support operation on medical apparatuses, other than X-ray diagnostic apparatuses, for example, X-ray CT apparatuses, ultrasonic diagnostic apparatuses, medical image display apparatuses, and medical image processing apparatuses.

In addition, the user interface apparatus 3 may include an operation means other than the track pad 33. When letting the user interface apparatus 3 have a function as a pointing device like the track pad 33, it is possible to use, for example, a joystick, in place of the track pad 33, which instructs an operation direction and an operation amount in accordance with the tilt of the stick. Pressure-sensitive buttons and the like may be arranged on the user interface apparatus 3 in place of or together with the track pad 33.

In addition, the second embodiment has exemplified the case in which the acceleration sensor detects the posture of the user interface apparatus 3. However, other arrangements may be used as means for detecting the posture of the user interface apparatus 3. For example, the user may select the posture of the user interface apparatus 3 before the start of a surgery by operating the user interface apparatus 3 or the console unit 134.

The second embodiment has also exemplified the case in which the horizontal direction represented by the signal transmitted from the user interface apparatus 3 is reversed on the premise that the vertical direction DUy viewed from the user coincides with the vertical direction DIy of the user interface apparatus 3. If, however, the vertical direction DUy viewed from the user does not coincide with the vertical direction DIy of the user interface apparatus 3, the vertical direction represented by the signal transmitted from the user interface apparatus 3 may be reversed. In this case, it is not necessary to reverse the horizontal direction. In addition, the correction performed by the correction system 104 is not limited to the processing of reversing a direction, and may include the processing of increasing/decreasing the operation amount in dragging operation or the like in accordance with a tilt relative to the gravitational direction of the user interface apparatus 3.

It is possible to provide a holding mechanism, which holds the user interface apparatus 3, on the obverse surface side of lead protective clothing worn inside a sterile gown and attach the user interface apparatus 3 to the user by using the holding mechanism instead of providing the pocket 305 on the sterile gown 300 and attaching the user interface apparatus 3 to the user. Even in this case, it is possible to operate the user interface apparatus 3 from the obverse surface side of the sterile gown as in the case in which the user interface apparatus 3 is accommodated in the pocket 305.

While certain embodiments have been described, these embodiments have been presented by way of example only, and are not intended to limit the scope of the inventions.

Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical work support system, comprising:
a plurality of interface apparatuses, each including a track pad and an acceleration sensor configured to detect a gravitational acceleration of the interface apparatus, each being assigned to an identifier, and each being configured to receive input only from the track pad, the track pad being configured to accept a control operation from a user via the track pad to control a medical apparatus, and output a signal corresponding to the control operation and including the identifier of a respective interface apparatus of the plurality of interface apparatuses;
a wireless communication circuitry configured to wirelessly receive the signal and the detected acceleration from each of the plurality of interface apparatuses; and
processing circuitry configured to:
determine that a particular interface apparatus of the plurality of interface apparatuses has an operation right for operating the medical apparatus that is an operation target to be operated by the particular interface apparatus, based on association of the identifier of the particular interface apparatus with the operation right,
select a particular signal transmitted from the particular interface apparatus having the operation right, out of the signals transmitted from the plurality of interface apparatuses based on the identifier of the particular interface apparatus included in the particular signal, and transmit the particular signal to the medical apparatus only when the particular interface apparatus has the operation right,
determine that a first interface apparatus of the plurality of interface apparatuses having no operation right requests the operation right for the medical apparatus that is the operation target, based on a signal received from the first interface apparatus which corresponds to a specific operation and includes an identifier of the first interface apparatus, the specific operation being an operation performed by a user and received by the first interface apparatus via the corresponding track pad and including a predetermined sequence of rubbing the corresponding track pad a predetermined number of times in a predetermined direction within a predetermined period of time,
give the operation right to the first interface apparatus by associating the identifier of the first interface apparatus with the operation right, and
determine a mode in which the first interface apparatus is used based on the detected acceleration as compared with a threshold,
wherein each of the plurality of interface apparatuses is detachably provided on a reverse surface side of a sterile gown that the user wears or inside a pocket of the gown, and the specific operation is received on the corresponding track pad of the first interface apparatus from an obverse surface side of the sterile gown.

2. The medical work support system according to claim 1, wherein the processing circuitry is further configured to make a notice of the particular interface apparatus of the plurality of interface apparatuses currently having the operation right.

3. The medical work support system according to claim 1, wherein:
the acceleration sensor is configured to detect a posture of each interface apparatus of the plurality of interface apparatuses,
each interface apparatus is further configured to accept a direction operation designating a direction used to control the medical apparatus, and output a signal representing the designated direction, and
the processing circuitry is further configured to perform correction of the designated direction represented by the signal in accordance with the posture detected by the acceleration sensor.

4. The medical work support system according to claim 3, wherein the processing circuitry is further configured to reverse the designated direction represented by the signal to a different direction in accordance with the posture detected by the acceleration sensor.

5. The medical work support system of claim 1, wherein the predetermined sequence is not part of any of a plurality of control operations to control the medical apparatus.

6. The medical work support system of claim 1, wherein the mode in which the first interface apparatus is used is a vertical mode.

7. The medical work support system of claim 1, wherein the mode in which the first interface apparatus is used is a horizontal mode.

* * * * *